United States Patent [19]

Ford et al.

[11] 4,314,083

[45] Feb. 2, 1982

[54] PREPARATION OF LINEAR POLYALKYLENE POLYAMINES

[75] Inventors: Michael E. Ford, Trexlertown; Thomas A. Johnson, Orefield, both of Pa.

[73] Assignee: Air Products and Chemicals, Inc., Allentown, Pa.

[21] Appl. No.: 193,762

[22] Filed: Oct. 3, 1980

[51] Int. Cl.$^3$ ............................................. C07C 85/06
[52] U.S. Cl. ..................................... 564/479; 564/480
[58] Field of Search ........................ 564/479, 480, 478

[56] References Cited

U.S. PATENT DOCUMENTS

| | | | |
|---|---|---|---|
| 2,073,671 | 3/1937 | Andrews | 564/480 X |
| 2,098,289 | 11/1937 | Greenewalt | 564/479 |
| 3,387,032 | 6/1968 | Leonard | 564/480 X |
| 3,475,344 | 10/1969 | Adam et al. | 564/480 X |
| 3,708,539 | 1/1973 | Fenton | 564/480 |
| 3,714,259 | 1/1973 | Lichtenwalter et al. | 564/480 |
| 3,751,474 | 8/1973 | Phillips et al. | 564/479 X |
| 3,767,709 | 10/1973 | Fenton | 564/479 X |
| 4,036,881 | 7/1977 | Brennan et al. | 564/479 X |
| 4,044,053 | 8/1977 | Brennan et al. | 564/480 |
| 4,076,649 | 2/1978 | Baron | 564/479 X |
| 4,153,581 | 5/1979 | Habermann | 564/479 X |

Primary Examiner—John Doll
Attorney, Agent, or Firm—Russell L. Brewer; E. Eugene Innis; James C. Simmons

[57] ABSTRACT

A process for selectively preparing predominantly non-cyclic polyalkylene polyamine compounds are disclosed wherein an alkylene polyamine compound is contacted with a hydroxy compound in the presence of a catalytically effective amount of a salt of a nitrogen or sulfur containing substance or the corresponding acid at a temperature of from 250° to 300° C. under a pressure sufficient to maintain the reaction mixture essentially in liquid phase. The polyalkylene polyamine thus formed is recovered from the reaction mixture.

16 Claims, No Drawings

4,314,083

PREPARATION OF LINEAR POLYALKYLENE POLYAMINES

TECHNICAL FIELD

This invention relates to the preparation of polyalkylene polyamines.

BACKGROUND OF PRIOR ART

One of the early techniques for preparing linear polyalkylene polyamine compounds, such as diethylenetriamine and triethylene tetramine and higher homologues, has been to react an alkyl halide with an amine such as ammonia, ethylenediamine and the like at elevated temperatures and pressures. Generally, high yields of cyclic polyethylene polyamines, e.g. piperazine, triethylenediamine as well as other cyclic amines were produced. Another problem in the process was that hydrohalide salts of ammonia or hydrogen chloride were produced by the reaction, and thus expensive corrosion resistant equipment was required. U.S. Pat. No. 3,751,474 is representative.

More recently a series of patents disclosed the preparation of linear polyalkylene polyamine compounds by reacting a diol or an alkanolamine compound with an alkylenediamine compound under preselected process conditions to produce linear alkylene polyamines. These include:

U.S. Pat. No. 3,714,259, which shows preparing linear poly(ethylene)amines by contacting ethanolamine with an ethylendiamine compound in the presence of hydrogen and hydrogenation catalyst. An example of a hydrogenation catalyst is nickel containing copper and chromium components;

U.S. Pat. No. 4,036,881, which shows the preparation of polyalkylene polyamines by reacting an alkanolamine with an alkylene amine compound in the presence of a phosphorous-containing substance selected from the group consisting of acidic metal phosphates, phosphoric acid compounds and hydrides and phosphate esters; and U.S. Pat. No. 4,044,053, which is somewhat similar to the '881 patent except that the alkylene amine compound is present in an excess amount and a diol is used in place of the alkanolamine.

SUMMARY OF THE INVENTION

It has been found that non-cyclic or linear polyalkylene polyamines are produced in high yield directly by reacting an alkylene amine compound and an alkanolamine in the presence of a catalytically effective amount of a salt of a substance containing nitrogen or sulfur, or the corresponding acid at temperatures of from 250°–350° C. under a pressure sufficient to maintain the mixture in liquid phase.

DETAILED DESCRIPTION OF THE INVENTION

Briefly, the invention relates to a process for synthesizing predominantly non-cyclic polyalkylene polyamines, and preferably predominantly linear polyethylene polyamines such as diethylenetriamine and higher homologues. In the process an alkylene amine having two primary amino groups, and preferably an unbranched alkylene moiety such as ethylene diamine, is reacted with an alkanolamine having a primary or secondary hydroxy moiety and a primary amine group. Preferably, the alkanolamine has an unbranched alkylene moiety.

The alkylene amine reactants that can be used in practicing the process are represented by the general formula:

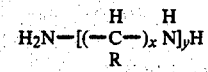

where R is a hydrogen or a lower alkyl ($C_{1-4}$) radical, X is a number from 2 to about 6, and Y is a number from 1 to about 4. Examples of alkylene diamine compounds suited for the reaction include 1,3-propylenediamine, diethylenetriamine, triethylenetetramine and ethylenediamine which is the preferred alkylene diamine composition.

The alkanolamine compounds which are used in practicing the process include those represented by the formula:

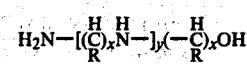

wherein R is hydrogen or a lower alkyl $C_{1-4}$ radical; X is a number from 2 to about 6; and Y is a number from 0 to 3. Examples of alkanolamine compounds that can be used are ethanolamine, isomeric propanolamines, N-(2-aminoethyl) piperazine and ethanolamine.

The polyalkylene amines that are produced by the reaction of an alkylenediamine and an alkanolamine or diol then are represented by the formula:

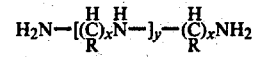

wherein R is hydrogen or a lower alkyl ($C_{1-4}$) radical; X is a number from 2 to about 6; and Y is a number from 2 to about 6. Examples of linear polyalkylene polyamines that are produced include tributylenetetramine, diethylenetriamine, triethylenetetramine and tetraethylenepentamine.

The catalysts which are suited for practicing the process described herein are the metal salts of nitrogen and sulfur-containing compounds and their corresponding acids. With respect to nitrogen-containing substances, the salts are of nitrates and the corresponding acids typically inorganic nitrates. Virtually any metal salt of the nitrate can be used, and these generally include Group 1, 2, 3a, 4, 6b–8b metals and include hydrogen, ammonium ion, lithium, sodium, potassium, beryllium, magnesium, chromium, manganese, iron, cobalt, zinc, aluminum, antimony, bismuth, tin, ammonium ion and boron. Hydrogen and the ammonium ion are deemed Group 1 metals for purposes of this invention. Nitrites, when used, are converted to nitrates and, for purposes herein, are deemed nitrates.

With respect to the catalytic substance containing sulfur, such compounds include sulfates and the corresponding acid. With respect to the sulfates, typically inorganic sulfates, the metals specified with respect to the nitrogen-containing substances are also suited and these include the ammonium ion and hydrogen.

The above-mentioned nitrogen and sulfur-containing substances are not intended to be exhaustive of those which may be employed as a catalyst material. However, as might be expected, it is preferred to use those which are more reactive and provide for substantial conversion with high selectivity to the product. Specific examples of catalytic materials which are effective at low levels include nitric acid, beryllium nitrate, boron nitrate, iron nitrate, aluminum nitrate, bismuth nitrate, sulfuric acid, beryllium sulfate, iron sulfate, ammonium sulfate, boron sulfate, and aluminum sulfate.

The quantity of nitrogen and sulfur-containing substance is somewhat empirical and can vary widely depending upon the reactivity of the catalyst and the reactivity of the reactants present. Usually, though, the amount used to provide a catalytic effect ranges from about 0.01 to 20% mole percent based upon the amount of the alkylenediamine compound present in the reaction mixture, and preferably in an amount of from about 0.5 to 8 mole percent based on the amount of alkylenediamine compound. Within these ranges though, the level of catalyst again is somewhat empirical and is adjusted depending on the product state desired. It has been found that as the reactivity of the catalyst increases and conversion increases, selectivity is reduced. In those instances where there is substantial catalytic activity, then, the quantity of catalyst is reduced to increase selectivity with a concomitant reduction in conversion.

In the preparation of linear polyalkylene polyamines, and preferably the linear polyethylene polyamines, the reaction is maintained at a temperature of from about 225° to about 350° C., and preferably from about 275° to 300° C. The pressure utilized for carrying out the reaction is that sufficient to maintain the reaction in essentially liquid phase which normally ranges from about 800 to 2500 psig. When utilizing these temperatures and pressures, the reaction is allowed to proceed until a desired conversion is obtained or reaction is complete. Normally the reaction is carried out within about 1 to 2 hours.

It is important in carrying out the process that the proportion of alkylenediamine compound to alkanolamine compound, be in a stoichiometric excess, e.g. to 10:1, to result in highest selectivity to linear product. When the alkylene diamine compound approaches a 1:1 molar ratio, on a weight basis with the alkanolamine, or falls below that level then the alkanolamine may have a tendency to form the cyclic amine compositions. Generally, the mole ratio of alkylenediamine compound to alkanolamine compound is from about 0.3 to 5, and preferably about 0.5 to 2:1.

Recovery of the linear polyalkylene polyamines from the reaction mixture can be accomplished by conventional techniques, these techniques generally involving a distillation reaction. Often a small amount of a salt, such as the one used as the catalytic material, is added to the polyalkylene polyamine separation purification as described in U.S. Pat. No. 3,755,447.

The following examples illustrate the nature of the process described herein that are not intended to limit the scope of the invention.

EXAMPLES 1-9

A series of runs 1-8 were made to produce linear polyethylene polyamines by the reaction of ethylenediamine and ethanolamine in a mole ratio of 1:2 in the presence of nitrogen-containing catalysts. The reaction was carried out in a 2 milliliter shaker reactor at a pressure of 1,000 psig and a temperature of 300° C. Each reaction was carried out for about two hours. At the completion of the reaction, the contents were cooled and the reaction mixture analyzed by gas-liquid chromotography.

Run 9 attempted to duplicate the art as taught by U.S. Pat. No. 4,036,881, which used boron phosphate as the catalyst. This was used for comparative purposes.

Tables 1 and 2 show results in terms of the amount of polyamines produced by the reaction. Conversion and selectivity are specified. As noted, the catalytic component was varied and the amount varied on the basis of weight mole percent of the alkylenediamine.

TABLE 1

POLYETHYLENE AMINES FROM ETHYLENEDIAMINE AND ETHANOLAMINE[a]

| Run | Catalyst | Level Mole % | Temp. °C. | PIP | TEDA | DETA | AEP | TAEA | TETA | BAEP | PEEDA | AE-TETA | TEPA | AE-BAEP | AE-PEEDA |
|---|---|---|---|---|---|---|---|---|---|---|---|---|---|---|---|
| 1 | nitric acid | 5.0 | 300 | — | 0.27 | 9.04 | 4.28 | 0.30 | 1.78 | 3.95 | 1.69 | 24.53 | — | 2.37 | — |
| 2 | lithium nitrate | 5.0 | 300 | — | 0.23 | 7.07 | 5.42 | 0.92 | 3.06 | 6.42 | 4.16 | 20.36 | — | 1.49 | — |
| 3 | beryllium nitrate | 5.0 | 300 | 4.69 | 0.06 | 5.02 | 2.80 | 0.38 | 1.78 | 2.40 | 1.04 | 20.38 | 0.20 | 4.58 | — |
| 4 | boron nitrate | 2.5 | 300 | 8.19 | 0.94 | 4.35 | 4.62 | 0.29 | 0.54 | 1.61 | 1.44 | 14.06 | — | 6.53 | — |
| 5 | iron nitrate | 2.5 | 300 | 4.75 | 0.27 | 3.30 | 3.02 | 0.49 | 1.09 | 2.58 | 1.30 | 20.23 | — | 4.72 | — |
| 6 | aluminum nitrate | 2.5 | 300 | 4.62 | 0.66 | 4.96 | 4.10 | 1.10 | 2.61 | 3.14 | 2.55 | 23.17 | — | 5.32 | — |
| 7 | bismuth nitrate | 2.5 | 300 | — | 0.36 | 5.51 | 3.55 | 0.19 | 1.75 | 3.67 | 2.05 | 34.14 | — | 4.07 | — |
| 8 | ammonium | 4.8 | 300 | 2.90 | — | 0.51 | 2.86 | — | 1.05 | 1.10 | 0.69 | — | 1.09 | 0.20 | — |

TABLE 1-continued
POLYETHYLENE AMINES FROM ETHYLENEDIAMINE AND ETHANOLAMINE[a]

| Run | Catalyst | Level Mole % | Temp. °C. | PIP | TEDA | DETA | AEP | TAEA | TETA | BAEP | PEEDA | AE-TETA | TEPA | AE-BAEP | AE-PEEDA |
|---|---|---|---|---|---|---|---|---|---|---|---|---|---|---|---|
| | nitrate | | | | | | | | | | | | | | |

[a] All numbers refer to weight percent of individual components in the product mixture on a feedstock-free basis.
PIP—Piperazine
TEDA—Triethylene diamine
DETA—Diethylenetriamine
AEP—Aminoethylpiperazine
TAEA—Tris(aminoethyl)amine
TETA—Triethylenetetramine
BAEP—N,N[1]-Bis(aminoethyl)piperazine
PEEDA—N-(Piperazinoethyl)ethylenediamine
AE-TETA—N-(Aminoethyl)triethylenetetramine
TEPA—Tetraethylenepentamine
AE-BAEP—N-(2-(2-aminoethylamino)-N[1]-(2-aminoethyl)piperazine
AE-PEEDA—N-(2-Piperazinoethyl)diethylenetriamine

TABLE 2
COMPARISON OF NITROGEN AND PHOSPHOROUS CATALYSTS

| Example | Catalyst | Level[a] | Conversion[b] | Selectivity[c] |
|---|---|---|---|---|
| 1 | Nitric Acid | 5.0 | 37.2 | 73.9 |
| 2 | Lithium Nitrate | 5.0 | 26.2 | 63.9 |
| 3 | Beryllium Nitrate | 5.0 | 63.2 | 64.1 |
| 4 | Boron Nitrate | 2.5 | 75.0 | 45.2 |
| 5 | Iron Nitrate | 2.5 | 71.2 | 60.2 |
| 6 | Aluminum Nitrate | 2.5 | 74.5 | 61.8 |
| 7 | Bismuth Nitrate | 2.5 | 52.0 | 75.2 |
| 8 | Ammonium Nitrate | 4.8 | 55.1 | 25.1 |
| 9 | Boron Phosphate | 5.0 | 94.9 | 31.0 |

[a] Mole percent of catalyst included, based on total amine feed.
[b] Weight percent of ethylenediamine and ethanolamine consumed in the reaction.
[c] Weight percent of noncyclic polyethylene amine products formed based on total reaction product.

Tables 1 and 2 show that the nitrogen containing catalysts were effective in producing a variety of linear polyalkylene polyamines. Iron, aluminum, lithium and bismuth nitrates gave good yields of polyalkylene polyamines with good conversion. As compared to the prior art catalyst, boron phosphate, selectivity was better in almost every case, ammonium nitrate being less effective. Although conversions were not as high as with boron phosphate conversions were good.

EXAMPLES 10-13

A series of runs 10-13 and similar to the previous examples were made to produce linear polyethylene polyamines by the reaction of ethylenediamine and ethanolamine except that a mole ratio of 1:1, a lower catalyst level and a pressure of 1200 psig was used. At the completion of the reaction, the contents were cooled and the reaction mixture analyzed by gas-liquid chromatography.

Run 14 corresponds to Example 9, which provides a comparison with the nitrates only using 2.5 mole percent boron phosphate.

Tables 3 and 4 show results in terms of the amount of polyamines produced by the reaction.

TABLE 3
POLYETHYLENE AMINES FROM ETHYLENEDIAMINE AND ETHANOLAMINE[a]

| Run | Catalyst | level mole % | Temp. °C. | PIP | TEDA | DETA | AEP | TAEA | TETA | BAEP | PEEDA | AE-TETA | TEPA | AE-BAEP | AE-PEEDA |
|---|---|---|---|---|---|---|---|---|---|---|---|---|---|---|---|
| 10 | iron nitrate | 2.5 | 300 | 0.40 | 0.15 | 5.91 | 1.36 | 0.50 | 2.86 | 0.80 | — | — | — | — | — |
| 11 | aluminum nitrate | 2.5 | 300 | 2.52 | — | 4.28 | 1.66 | 0.36 | 1.26 | 0.25 | 0.51 | — | — | 0.13 | — |
| 12 | bismuth nitrate | 2.5 | 300 | 2.22 | — | 0.08 | 0.08 | 0.42 | 1.82 | 0.12 | 0.46 | — | — | — | — |
| 13 | beryllium nitrate | 5.0 | 300 | 1.76 | — | 2.43 | 1.42 | 0.43 | 0.79 | 0.55 | 1.42 | 0.11 | 0.11 | 0.03 | — |

[a] All numbers refer to weight percent of individual components in the product mixture on a feedstock-free basis.
PIP—Piperazine
TEDA—Triethylene diamine
DETA—Diethylenetriamine
AEP—Aminoethylpiperazine
TAEA—Tris(aminoethyl)amine
TETA—Triethylenetetramine
BAEP—N,N[1]-Bis(aminoethyl)piperazine
PEEDA—N-(Piperazinoethyl)ethylenediamine
AE-TETA—N-(Aminoethyl)triethylenetetramine
TEPA—Tetraethylenepentamine
AE-BAEP—N-(2-(2-aminoethylamino)-N[1]-(2-aminoethyl)piperazine
AE-PEEDA—N-(2-Piperazinoethyl)diethylenetriamine

TABLE 4
Comparison of Nitrogen and Phosphorous Catalysts

| Example | Catalyst | Level[a] | Conversion[b] | Selectivity[c] |
|---|---|---|---|---|
| 10 | Iron Nitrate | 2.5 | 39.8 | 77.2 |
| 11 | Aluminum Nitrate | 2.5 | 60.3 | 53.8 |
| 12 | Bismuth Nitrate | 2.5 | 49.4 | 43.7 |
| 13 | Beryllium Nitrate | 5.0 | 69.5 | 45.7 |

TABLE 4-continued

Comparison of Nitrogen and Phosphorous Catalysts

| Example | Catalyst | Level[a] | Conversion[b] | Selectivity[c] |
|---------|----------|----------|---------------|----------------|
| 14 | Boron Phosphate | 2.5 | 76.9 | 45.0 |

[a]Mole percent of catalyst included, based on total amine feed.
[b]Weight percent of ethylenediamine and ethanolamine consumed in this reaction.
[c]Weight percent of noncyclic polyethylene amine products formed based on total reaction product.

Again, the tables show that the nitrate salts provided good yields of polyethylene polyamines, as compared to the prior art boron phosphate. As compared to the results in Tables 1 and 2, it can be seen that conversion decreased slightly for the same catalyst and that selectivity also decreased slightly. Selectivity would be expected to decrease as compared to the runs in Examples 1–8 since the ethanolamine concentration is higher and it can react with itself to form cyclics.

EXAMPLES 15–22

A series of runs similar to the previous examples were made to produce linear polyethylene polyamines except that a mole ratio of ethylenediamine and ethanolamine of 1:2, sulphur-containing catalysts at various levels, and a pressure of 1,000 psig was used. Each reaction was carried out for about two hours. At the completion of the reaction, the contents were cooled and the reaction mixture analyzed by gas-liquid chromatography.

Example 23 provides a comparison with boron phosphate at low levels.

Tables 5 and 6 show results in terms of the amount of polyamines produced by the reaction.

TABLE 6

Comparison of Sulfate and Phosphate Catalysts

| Example | Catalyst | Level[a] | Conversion[b] | Selectivity[c] |
|---------|----------|----------|---------------|----------------|
| 15 | Sulfuric Acid | 1.67 | 42.9 | 54.8 |
| 16 | Ammonium Sulfate | 1.75 | 66.1 | 40.5 |
| 17 | Aluminum | 0.45 | 25.5 | 36.6 |
| 18 | Boron Sulfate | 0.62 | 40.3 | 71.0 |
| 19 | Boron Sulfate | 2.50 | 55.9 | 54.6 |
| 20 | Ammonium Sulfate | 0.60 | 51.9 | 45.3 |
| 21 | Iron Sulfate | 2.50 | 31.4 | 63.4 |
| 22 | Beryllium Sulfate | 5.00 | 46.0 | 47.1 |
| 23 | Boron Phosphate | 0.80 | 50.9 | 66.0 |
| 9 | Boron Phosphate | 5.00 | 94.9 | 31.0 |

[a]Mole percent of catalyst included, based on total amine feed.
[b]Weight percent of ethylenediamine and ethanolamine consumed in the reaction
[c]Weight percent of noncyclic polyethylene amine products formed.

The results in Tables 5 and 6 clearly show that sulfur containing catalysts including sulfuric acid are effective for producing linear polyethylamine polyamines from the reaction of ethylene diamine and ethanolamine. Boron sulfate gave extremely high selectivity at a low level, e.g. 0.62 mole percent ethylenediamine. Surprisingly, with the sulfate catalyst higher concentration of catalyst resulted in substantially reduced selectivity with only modest improvements in conversion, see boron sulfate. Boron phosphate, on the other hand, experienced a doubling in conversion while selectivity dropped in half.

TABLE 5

POLYETHYLENE AMINES FROM ETHYLENEDIAMINE AND ETHANOLAMINE[a]

| Run | Catalyst | level mole % | Temp. °C. | PIP | TEDA | DETA | AEP | TAEA | TETA | BAEP | PEEDA | AE-TETA | TEPA | AE-BAEP | AE-PEEDA |
|-----|----------|--------------|-----------|-----|------|------|-----|------|------|------|-------|---------|------|---------|----------|
| 15 | sulfuric acid | 1.67 | 300 | — | 1.35 | 17.80 | 13.56 | 1.63 | 5.17 | 3.75 | 3.50 | 5.38 | 0.19 | 2.31 | 0.47 |
| 16 | ammonium sulfate | 1.75 | 300 | 5.36 | 0.92 | 4.91 | 5.21 | 0.18 | 1.54 | 2.36 | 3.04 | 7.85 | 1.59 | 4.89 | 1.86 |
| 17 | aluminum sulfate | 0.45 | 300 | 6.56 | 0.61 | 8.37 | 6.84 | 0.39 | 2.03 | 3.66 | 2.79 | 4.97 | 0.39 | 5.28 | 0.63 |
| 18 | boron sulfate | 0.62 | 300 | 0.10 | 1.49 | 27.30 | 5.63 | 0.64 | 5.31 | 2.50 | 2.55 | 5.51 | 2.80 | 3.87 | 0.79 |
| 19 | boron sulfate | 2.50 | 300 | 0.09 | 0.07 | 3.74 | 3.06 | — | 0.47 | 1.15 | 1.11 | 3.97 | — | 1.32 | — |
| 20 | ammonium sulfate | 0.60 | 300 | 5.26 | — | 11.69 | 8.72 | — | 3.61 | 1.61 | 2.00 | 0.46 | — | 1.48 | — |
| 21 | iron sulfate | 2.50 | 300 | — | 0.29 | 7.15 | 8.20 | 0.16 | 0.38 | 2.39 | 1.63 | 4.40 | — | 3.60 | — |
| 22 | beryllium sulfate | 5.0 | 300 | 5.76 | 0.96 | 10.31 | 6.95 | 0.37 | 1.66 | 1.70 | 1.48 | 4.60 | — | 1.96 | 0.20 |

[a]All numbers refer to weight percent of individual components in the product mixture on a feedstock-free basis.
PIP—Piperazine
TEDA—triethylene diamine
DETA—Diethylenetriamine
AEP—Aminoethylpiperazine
TAEA—Tris(aminoethyl)amine
TETA—Triethylenetetramine
BAEP—N,N'-Bis(aminoethyl)piperazine
PEEDA—N-(Piperazinoethyl)ethylenediamine
AE-TETA—N-(Aminoethyl)triethylenetetramine
TEPA—Tetraethylenepentamine
AE-BAEP—N-(2-(2-aminoethylamino)-N'-(2-aminoethyl)piperazine
AE-PEEDA—N-(2-Piperazinoethyl)diethylenetriamine

EXAMPLES 24–29

A series of runs similar to Examples 15–22 were made except that a mole ratio of diamine to alkanolamine of 1:1 was used in the presence of sulfur-containing catalysts.

Tables 7 and 8 show results in terms of the amount of polyamines produced by the reaction. Conversion and selectivity are specified.

TABLE 8-continued

Comparison of Sulfate and Phosphate Catalysts

| Example | Catalyst | Level[a] | Conversion[b] | Selectivity[c] |
|---|---|---|---|---|
| 23 | Phosphate Boron Phosphate | 0.8 | 50.9 | 66.0 |

[a]Mole percent of catalyst included, based on total amine feed.
[b]Weight percent of ethylenediamine and ethanolamine consumed in the reaction
[c]Weight percent of noncyclic polyethylene amine products formed.

TABLE 7

POLYETHYLENE AMINES FROM ETHYLENEDIAMINE AND ETHANOLAMINE[a]

| Run | Catalyst | level mole % | Temp. °C. | PIP | TEDA | DETA | AEP | TAEA | TETA | BAEP | PEEDA | AE-TETA | TEPA | AE-BAEP | AE-PEEDA |
|---|---|---|---|---|---|---|---|---|---|---|---|---|---|---|---|
| 24 | boron sulfate | 1.25 | 300 | 64.75 | — | 14.33 | 5.32 | — | 0.61 | 2.32 | — | — | — | — | — |
| 25 | boron sulfate | 2.50 | 300 | 7.14 | 0.08 | 2.38 | 10.17 | — | 0.19 | 4.00 | 5.89 | 3.88 | 1.46 | 4.53 | 0.26 |
| 26 | ammonium sulfate | 0.60 | 300 | 4.43 | — | 16.75 | 1.63 | 0.93 | 3.38 | 2.43 | 0.67 | — | — | — | 0.71 |
| 27 | ammonium sulfate | 1.75 | 300 | 4.15 | — | 5.91 | 1.02 | — | — | 0.31 | 0.72 | 0.64 | — | — | — |
| 28 | boron sulfate | 0.625 | 300 | — | 0.66 | 9.69 | 1.70 | — | 0.81 | 1.35 | 0.54 | 5.48 | — | 1.24 | — |
| 29 | sulfuric acid | 1.67 | 300 | — | 0.84 | 9.15 | 1.82 | 0.21 | 1.02 | 1.26 | 0.75 | 4.22 | — | 1.91 | — |

[a]All numbers refer to weight percent of individual components in the product mixture on a feedstock-free basis.
PIP—Piperazine
TEDA—triethylene diamine
DETA—Diethylenetriamine
AEP—Aminoethylpiperazine
TAEA—Tris(aminoethyl)amine
TETA—Triethylenetetramine
BAEP—N,N[1]-Bis(aminoethyl)piperazine
PEEDA—N-(Piperazinoethyl)ethylenediamine
AE-TETA—N-(Aminoethyl)triethylenetetramine
TEPA—Tetraethylenepentamine
AE-BAEP—N-(2-(2-aminoethylamino)-N[1]-(2-aminoethyl)piperazine
AE-PEEDA—N-(2-Piperazinoethyl)diethylenetriamine

TABLE 8

Comparison of Sulfate and Phosphate Catalysts

| Example | Catalyst | Level[a] | Conversion[b] | Selectivity[c] |
|---|---|---|---|---|
| 24 | Boron Sulfate | 1.25 | 26.3 | 17.1 |
| 25 | Boron Sulfate | 2.50 | 84.5 | 19.1 |
| 26 | Ammonium Sulfate | 0.60 | 46.1 | 31.4 |
| 27 | Ammonium Sulfate | 1.75 | 39.0 | 51.4 |
| 28 | Boron Sulfate | 0.625 | 25.9 | 74.5 |
| 29 | Sulfuric Acid | 1.67 | 34.5 | 68.9 |
| 14 | Boron | 2.50 | 76.9 | 45.0 |

These results show that generally selectivity to polyethylene polyamines increased as compared to Tables 5 and 6. This would be expected from the earlier work where selectivity is increased where the concentration of diamine vis-a-vis the ethanolamine increased. Conversions were slightly lower.

EXAMPLES 30–34

A series of runs similar to Runs 15–22 were made except that a mole ratio of 2:1 and a pressure of 1,500 psig was used.

Runs 35 and 36 provide a comparison with boron phosphate.

Tables 9 and 10 show results in terms of the amount of polyamines produced by the reaction.

TABLE 9

POLYETHYLENE AMINES FROM ETHYLENEDIAMINE AND ETHANOLAMINE[a]

| Run | Catalyst | level mole % | Temp. °C. | PIP | TEDA | DETA | AEP | TAEA | TETA | BAEP | PEEDA | AE-TETA | TEPA | AE-BAEP | AE-PEEDA |
|---|---|---|---|---|---|---|---|---|---|---|---|---|---|---|---|
| 30 | boron sulfate | 2.50 | 300 | 5.58 | 0.06 | 10.49 | 5.78 | 0.46 | 0.72 | 2.34 | 2.93 | 1.07 | — | 0.48 | — |
| 31 | boron sulfate | 1.25 | 300 | 3.08 | — | 10.85 | 1.26 | — | — | 1.02 | 0.61 | — | — | — | — |
| 32 | boron sulfate | 0.625 | 300 | — | 0.34 | 4.18 | 0.53 | — | — | 0.78 | 0.10 | 1.19 | — | — | — |
| 33 | ammonium sulfate | 1.75 | 300 | 5.96 | — | 9.79 | 1.68 | — | — | 1.35 | 0.84 | — | — | — | — |
| 34 | sulfuric | 1.67 | 300 | 10.58 | 0.19 | 8.53 | 1.08 | 0.10 | 1.32 | 0.87 | 0.41 | 0.87 | — | — | — |

TABLE 9-continued
POLYETHYLENE AMINES FROM ETHYLENEDIAMINE AND ETHANOLAMINE[a]

| Run | Catalyst | level mole % acid | Temp. °C. | PIP | TEDA | DETA | AEP | TAEA | TETA | BAEP | PEEDA | AE-TETA | TEPA | AE-BAEP | AE-PEEDA |
|---|---|---|---|---|---|---|---|---|---|---|---|---|---|---|---|

[a]All numbers refer to weight percent of individual components in the product mixture on a feedstock-free basis.
PIP—Piperazine
TEDA—triethylene diamine
DETA—Diethylenetriamine
AEP—Aminoethylpiperazine
TAEA—Tris(aminoethyl)amine
TETA—Triethylenetetramine
BAEP—N,N[1]-Bis(aminoethyl)piperazine
PEEDA—N-(Piperazinoethyl)ethylenediamine
AE-TETA—N-(Aminoethyl)triethylenetetramine
TEPA—Tetraethylenepentamine
AE-BAEP—N-(2-(2-aminoethylamino)-N[1]-(2-aminoethyl)piperazine
AE-PEEDA—N-(2-Piperazinoethyl)diethylenetriamine

TABLE 10
Comparison of Sulfate and Phosphate Catalysts

| Example | Catalyst | Level[a] | Conversion[b] | Selectivity[c] |
|---|---|---|---|---|
| 30 | boron Sulfate | 2.50 | 45.7 | 42.6 |
| 31 | Boron Sulfate | 1.25 | 34.4 | 64.5 |
| 32 | Boron Sulfate | 0.625 | 32.0 | 75.4 |
| 33 | Ammonium Sulfate | 1.75 | 21.4 | 49.9 |
| 34 | Sulfuric Acid | 1.67 | 41.5 | 45.2 |
| 35 | Boron Phosphate | 0.80 | 52.3 | 62.0 |
| 36 | Boron Phosphate | 5.00 | 66.2 | 43.0 |

[a]Mole percent of catalyst included, based on total amine feed.
[b]Weight percent of ethylenediamine and ethanolamine consumed in the reaction
[c]Weight percent of noncyclic polyethylene amine products formed.

What is claimed is:

1. A process for preparing a noncyclic polyalkylene polyamine comprising the steps of: contacting an alkyleneamine compound having two primary amino groups of the formula:

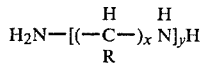

wherein R is hydrogen or a lower alkyl, x is a number from 2 to about 6, and y is a number from 1 to about 4 with a hydroxy compound having primary or secondary hydroxyl groups of the general formula:

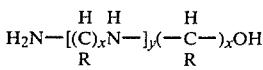

wherein R is hydrogen or a lower alkyl, x is a number from 2 to about 6; and y is a number from 0 to about 3; said contacting being performed in the presence of a catalytically effective amount of a salt of a substance of nitrogen or sulfur or their corresponding acids at temperatures sufficient to effect reaction between said alkyleneamine and said hydroxy compound under a pressure sufficient to maintain the reaction mixture essentially in liquid phase.

2. The process of claim 1 wherein said salt is of a nitrogen containing substance.

3. The process of claim 2 wherein said salt is an inorganic nitrate or nitric acid.

4. The process of claim 1 wherein the level of said catalytic substance is from about 0.01 to 2.0 mole percent based upon the amount of said alkyleneamine compound present in the reaction mixture.

5. The process of claim 3 wherein the temperature of the reaction is from about 225° to 350° C.

6. The process of claim 5 wherein the molar ratio of alkyleneamine compound to hydroxy compound is from about 0:3 to about 5.

7. The process of claim 5 wherein said nitrate is a nitrate of a Group 1, 2, 3a, 4, 6b and 8b metal.

8. The process of claim 6 wherein said nitrate is present in an amount from 0.5-8% mole percent of said alkyleneamine.

9. The process of claim 8 wherein said alkyleneamine compound is ethylenediamine, and said hydroxy compound is ethanolamine.

10. The process of claim 1 wherein said salt is of a sulfur containing substance.

11. The process of claim 10 wherein said sulfur containing substance is an inorganic sulfate or sulfuric acid.

12. The process of claim 1 wherein said temperature is from 225°-350° C.

13. The process of claim 11 wherein said catalyst is present in a proportion of from 0.01-20 mole percent of said alkylenediamine.

14. The process of claim 13 wherein said sulfate is a sulfate of a Group 1, 2, 3a, 4, 6b or 8b metal.

15. The process of claim 14 wherein said sulfate is present in a proportion of from 0.5-8 mole percent of said alkyleneamine.

16. The process of claim 15 wherein said alkyleneamine is ethylenediamine and said hydroxy compound is ethanolamine.

* * * * *